US011547849B2

(12) United States Patent
Hetke et al.

(10) Patent No.: US 11,547,849 B2
(45) Date of Patent: Jan. 10, 2023

(54) SYSTEMS AND METHODS FOR RUGGEDIZED PENETRATING MEDICAL ELECTRODE ARRAYS

(71) Applicant: NeuroNexus Technologies, Inc., Ann Arbor, MI (US)

(72) Inventors: Jamille Farraye Hetke, Brooklyn, MI (US); Rio J. Vetter, Plano, TX (US); Carlos Rackham, Plano, TX (US); Daryl R. Kipke, Dexter, MI (US)

(73) Assignee: NeuroNexus Technologies, Inc., Ann Arbor, MI (US)

( * ) Notice: Subject to any disclaimer, the term of this patent is extended or adjusted under 35 U.S.C. 154(b) by 366 days.

(21) Appl. No.: 16/001,866

(22) Filed: Jun. 6, 2018

(65) Prior Publication Data
US 2018/0353750 A1 Dec. 13, 2018

Related U.S. Application Data

(60) Provisional application No. 62/516,202, filed on Jun. 7, 2017.

(51) Int. Cl.
*A61N 1/05* (2006.01)
*A61B 5/00* (2006.01)
(Continued)

(52) U.S. Cl.
CPC .............. *A61N 1/0502* (2013.01); *A61B 5/24* (2021.01); *A61B 5/287* (2021.01); *A61B 5/686* (2013.01);
(Continued)

(58) Field of Classification Search
CPC ...... A61N 1/0502; A61N 1/05; A61N 1/0534; A61N 1/0587; A61N 1/0531;
(Continued)

(56) References Cited

U.S. PATENT DOCUMENTS 5,215,088 A 6/1993 Normann et al.
6,622,035 B1 9/2003 Merilainen et al.
(Continued)

FOREIGN PATENT DOCUMENTS

WO WO2014094512 6/2014

OTHER PUBLICATIONS

Patent Cooperation Treaty, European Patent Office, "International Search Report" for Application No. PCT/US2018/036529, dated Sep. 10, 2018, 3 pages.
(Continued)

*Primary Examiner* — Eun Hwa Kim
*Assistant Examiner* — Adam Z Minchella
(74) *Attorney, Agent, or Firm* — Haynes and Boone, LLP

(57) ABSTRACT

Systems and methods for ruggedized neural probes are provided. Such probes may be adapted for penetrating tissue. An exemplary ruggedized penetrating electrode array system includes an elongate shank having one or more electrodes disposed on at least one exterior surface thereof and a backend structure. A proximal end of the elongate shank is secured to the backend structure. The exemplary array system further includes an elongate carrier secured to the backend structure and extending away from the backend structure toward the distal end of the elongate shank, the elongate carrier being more rigid than the elongate shank. Methods for fabricating such an array system are also provided.

19 Claims, 13 Drawing Sheets

(51) Int. Cl.
*A61B 5/24* (2021.01)
*A61B 5/287* (2021.01)
*A61B 18/00* (2006.01)
*A61B 18/14* (2006.01)

(52) U.S. Cl.
CPC .............. *A61N 1/05* (2013.01); *A61N 1/0534* (2013.01); *A61N 1/0587* (2013.01); *A61B 5/6869* (2013.01); *A61B 18/1477* (2013.01); *A61B 2018/0016* (2013.01); *A61N 1/0531* (2013.01); *A61N 1/0551* (2013.01)

(58) Field of Classification Search
CPC ........ A61N 1/0551; A61B 5/24; A61B 5/287; A61B 5/686; A61B 5/6869; A61B 18/1477; A61B 2018/0016
See application file for complete search history.

(56) References Cited

U.S. PATENT DOCUMENTS

| | | |
|---|---|---|
| 7,781,195 B1 | 8/2010 | Heller et al. |
| 7,941,202 B2 | 5/2011 | Hetke et al. |
| 8,561,292 B2 | 10/2013 | Seymour et al. |
| 8,865,288 B2 | 10/2014 | Bhandari et al. |
| 8,972,026 B2 | 3/2015 | Kipke et al. |
| 9,254,168 B2 | 2/2016 | Palanker |
| 9,687,166 B2 | 6/2017 | Subramaniam et al. |
| 2004/0015219 A1 | 1/2004 | Francischelli |
| 2004/0054393 A1 | 3/2004 | Stemme et al. |
| 2005/0043726 A1 | 2/2005 | McHale et al. |
| 2006/0276866 A1 | 12/2006 | McCreery |
| 2007/0027512 A1 | 2/2007 | Chan et al. |
| 2007/0067007 A1* | 3/2007 | Schulman ............ A61N 1/0526 607/115 |
| 2007/0106143 A1 | 5/2007 | Flaherty |
| 2009/0118806 A1 | 5/2009 | Vetter et al. |
| 2009/0283425 A1 | 11/2009 | Clark et al. |
| 2009/0299167 A1* | 12/2009 | Seymour ................. A61B 5/24 600/372 |
| 2010/0029148 A1* | 2/2010 | Perlin .................. A61N 1/0529 439/884 |
| 2010/0041972 A1 | 2/2010 | Mason |
| 2010/0331935 A1* | 12/2010 | Tabada ..................... A61N 1/05 600/377 |
| 2011/0112591 A1* | 5/2011 | Seymour ................. A61B 5/24 600/377 |
| 2012/0138335 A1 | 6/2012 | Tathireddy et al. |
| 2014/0107446 A1 | 4/2014 | Tolosa et al. |
| 2014/0194719 A1* | 7/2014 | Frewin .................. A61B 5/291 600/377 |
| 2015/0119673 A1 | 4/2015 | Pellinen |
| 2015/0128413 A1* | 5/2015 | Vetter .................. A61N 1/0529 29/854 |
| 2015/0133761 A1 | 5/2015 | Vetter et al. |
| 2016/0131636 A1 | 5/2016 | Tandon et al. |
| 2016/0317802 A1 | 11/2016 | Saini et al. |
| 2017/0080210 A1 | 3/2017 | Mercanzini |
| 2018/0339156 A1* | 11/2018 | Nash .................. A61N 1/36185 |

OTHER PUBLICATIONS

Hooks, Darren A., Construction and Validation of a Plunge Electrode Array for Three-Dimensional Determination of Conductivity in the Heart, IEEE Transactions on Biomedical Engineering, Feb. 2008, vol. 55, No. 2, pp. 626-635.

* cited by examiner

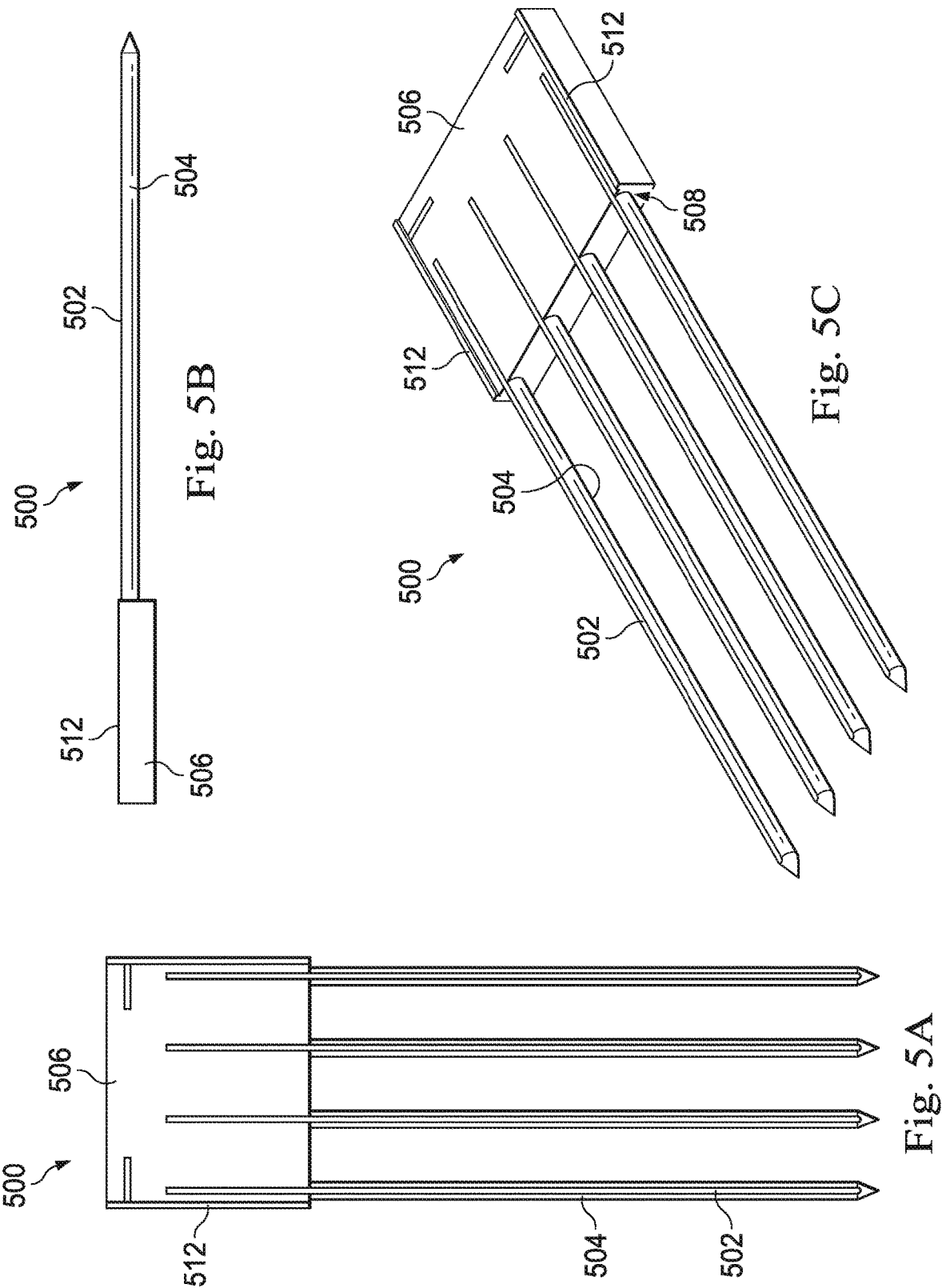

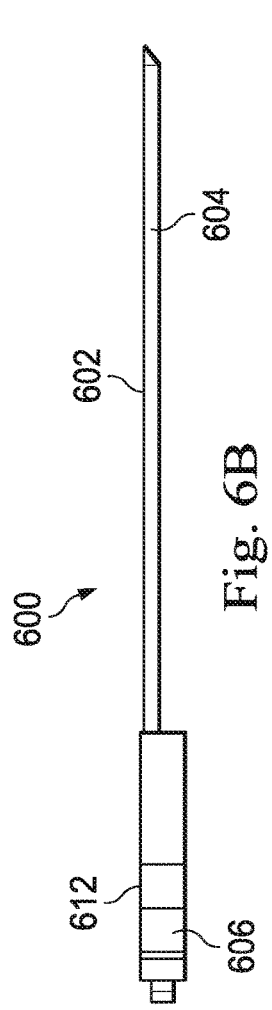
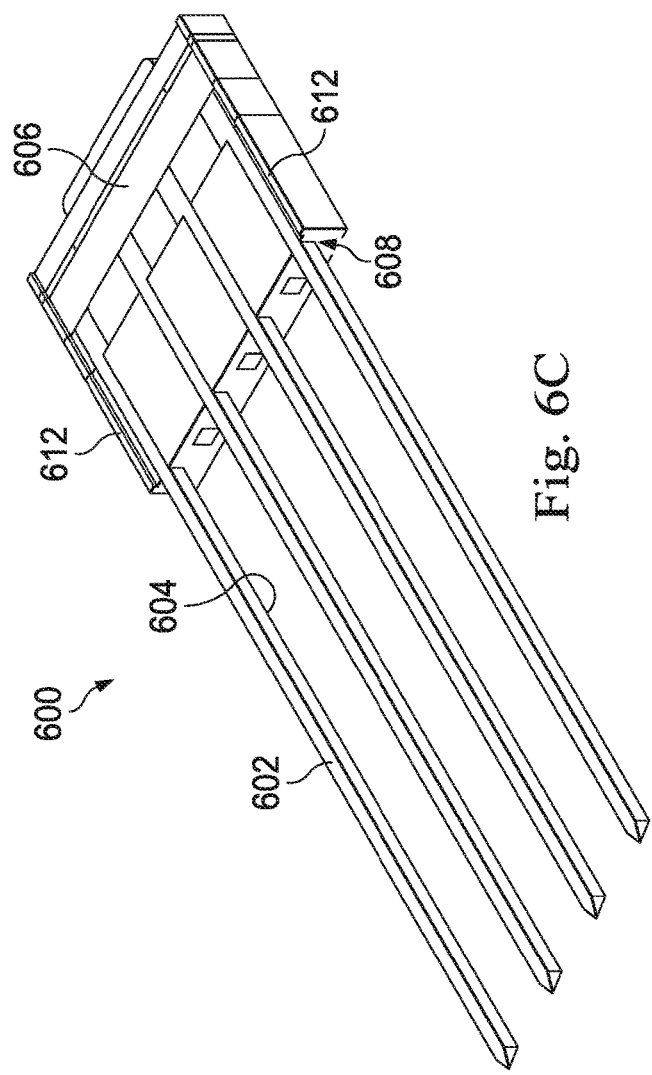
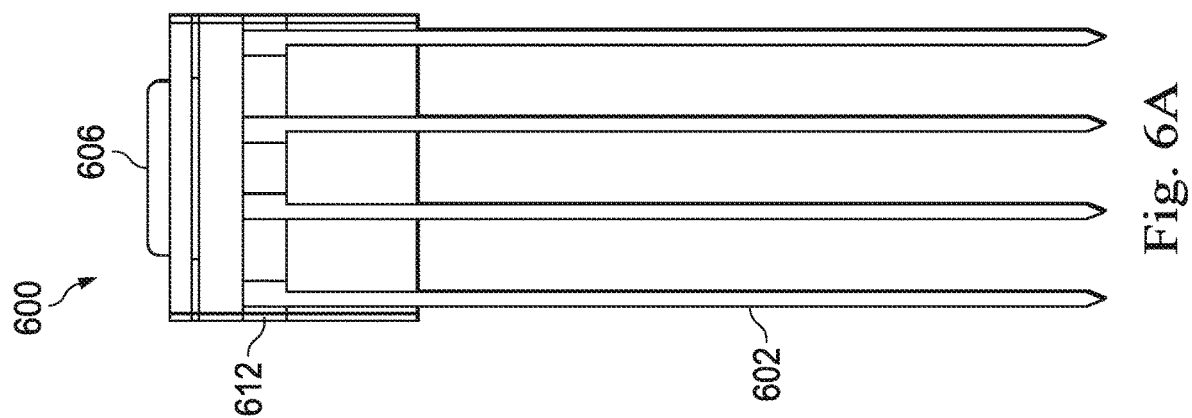

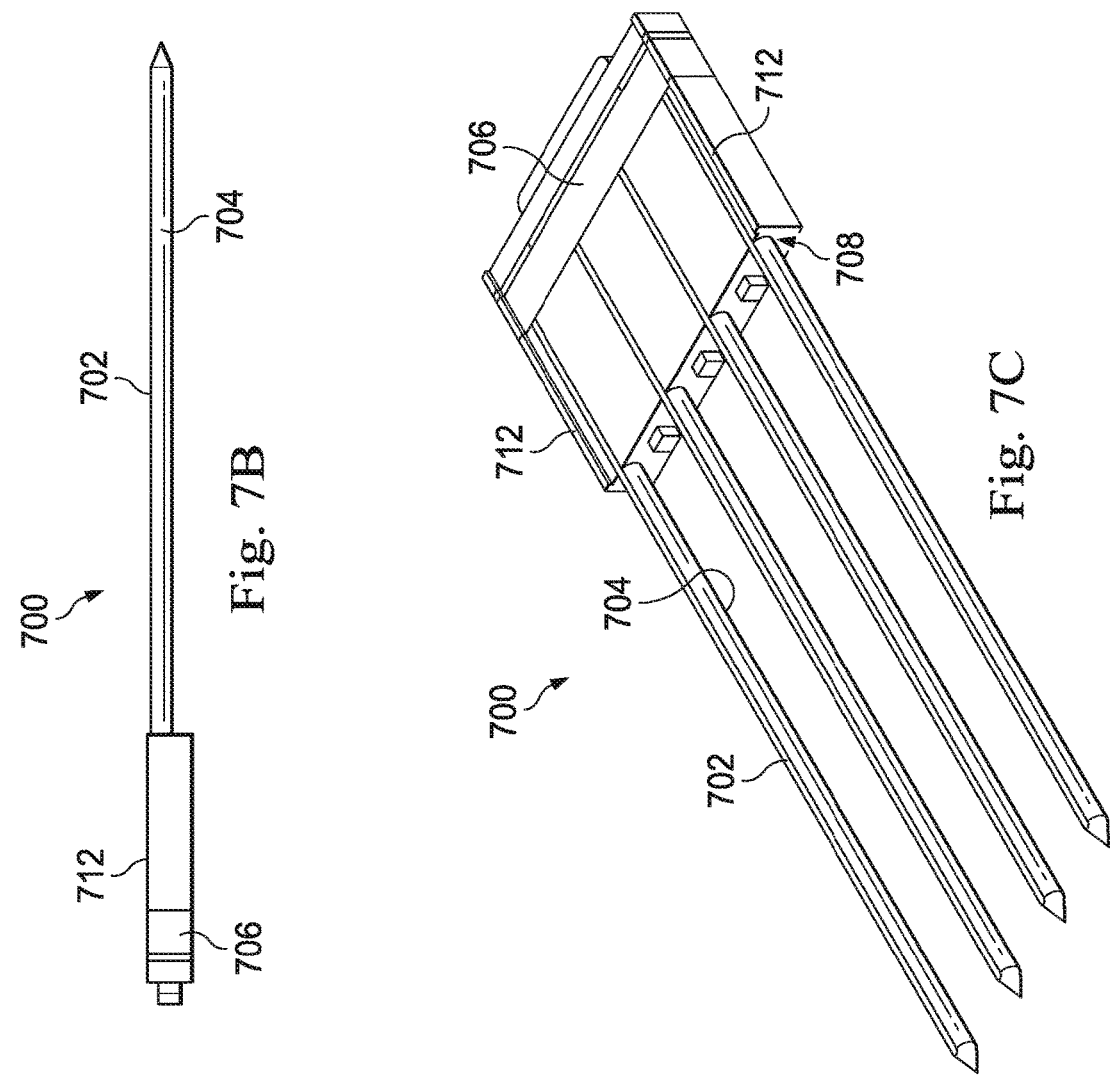

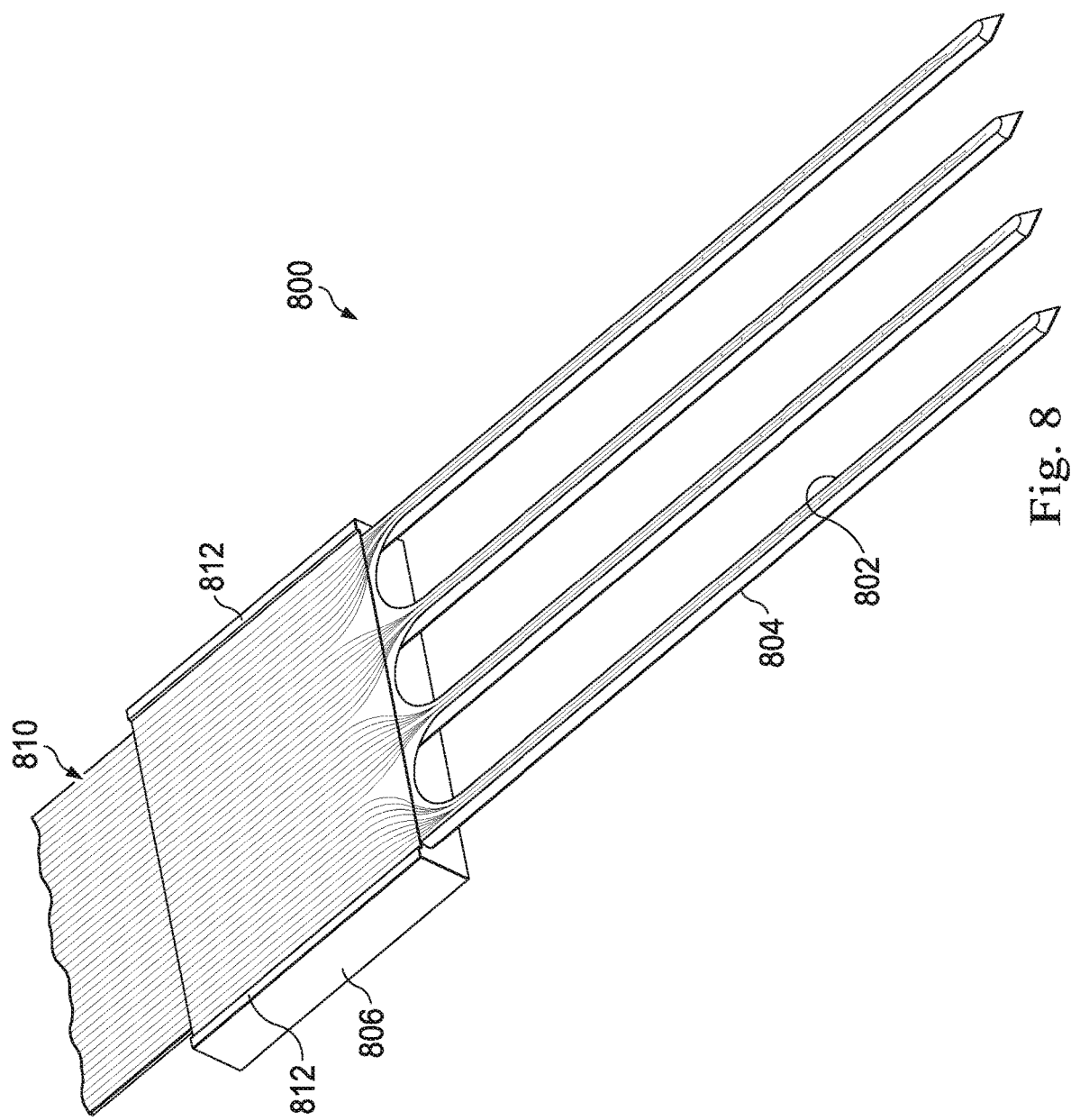

SYSTEMS AND METHODS FOR RUGGEDIZED PENETRATING MEDICAL ELECTRODE ARRAYS

CROSS-REFERENCE TO RELATED APPLICATION

This application claims the benefit of U.S. Provisional Application No. 62/516,202, filed Jun. 7, 2017, entitled "Systems and Methods for Ruggedized Penetrating Medical Electrode Arrays," the entire disclosure of which is hereby incorporated herein by reference.

FIELD

The present disclosure is directed to systems and methods for use in providing electrode arrays for medical applications, and more particularly to systems and methods for providing strong medical electrode arrays to penetrate into tougher tissues, such as cardiac tissue and neural tissue.

BACKGROUND

To interface with the nervous system, electrodes may be used, including multi-contact electrode arrays. Electrode arrays are designed to transmit signals into the tissue ("stimulation") or extract signals from the tissue ("sense"). These electrode arrays can be used in neuroscience and neurophysiological research as well as in clinical therapeutic and/or diagnostic applications. It is desirable to interface with the targeted volume in three-dimensions. Commercially available electrode arrays are limited in their ability to position electrode contacts in a three-dimensional arrangement. Two examples are the planar silicon array, often referred to as the "Michigan Probe" and an alternative silicon-based technology referred to as the "Utah Array." The Michigan Probe is limited to positioning electrode contacts in a two-dimensional arrangement, all within a single plane, which can subsequently be assembled into a three-dimensional structure. The Utah Array is also limited to positioning electrode contacts in a two-dimensional plane. Moreover, electrode contacts in a Utah Array are limited to placement on the tip of each electrode shank.

However, some current approaches to electrode array design may not be well adapted to penetrating tougher tissue, such as spinal cord, peripheral nerve, or muscle. For example, some currently available microelectrode arrays are too small and weak for insertion into tougher tissues, such as muscle.

SUMMARY

The embodiments of the invention are summarized by the claims that follow below.

In one embodiment, a ruggedized penetrating electrode array system includes a probe assembly, backend structure, and an elongate carrier. The elongate shank has one or more electrodes disposed on at least one exterior surface thereof. A proximal end of the elongate shank is secured to the backend structure. An elongate carrier is secured to the backend structure and extends away from the backend structure toward the distal end of the elongate shank. The elongate carrier is more rigid than the elongate shank.

In another embodiment, a neural probe electrode system includes a probe platform, a first probe array, and a backend structure. The probe platform is configured to receive at least one probe array. The first probe array has a first plurality of probes, each probe of the first plurality being supported by an elongate carrier that is more rigid than the probe. The backend structure is coupled to proximal ends of the first plurality of probes. The elongate carriers are secured to the backend structure.

In yet another embodiment, a method of fabricating a ruggedized penetrating electrode array system for insertion into tissue is provided. An electrode carrier body is patterned. An electrode body is fabricated. The electrode body is secured to the electrode carrier body, the electrode carrier body being more rigid than the electrode body. The electrode carrier body is affixed to a probe platform.

These embodiments and others may be better understood by reference to the accompanying drawings and detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

Figure 3:
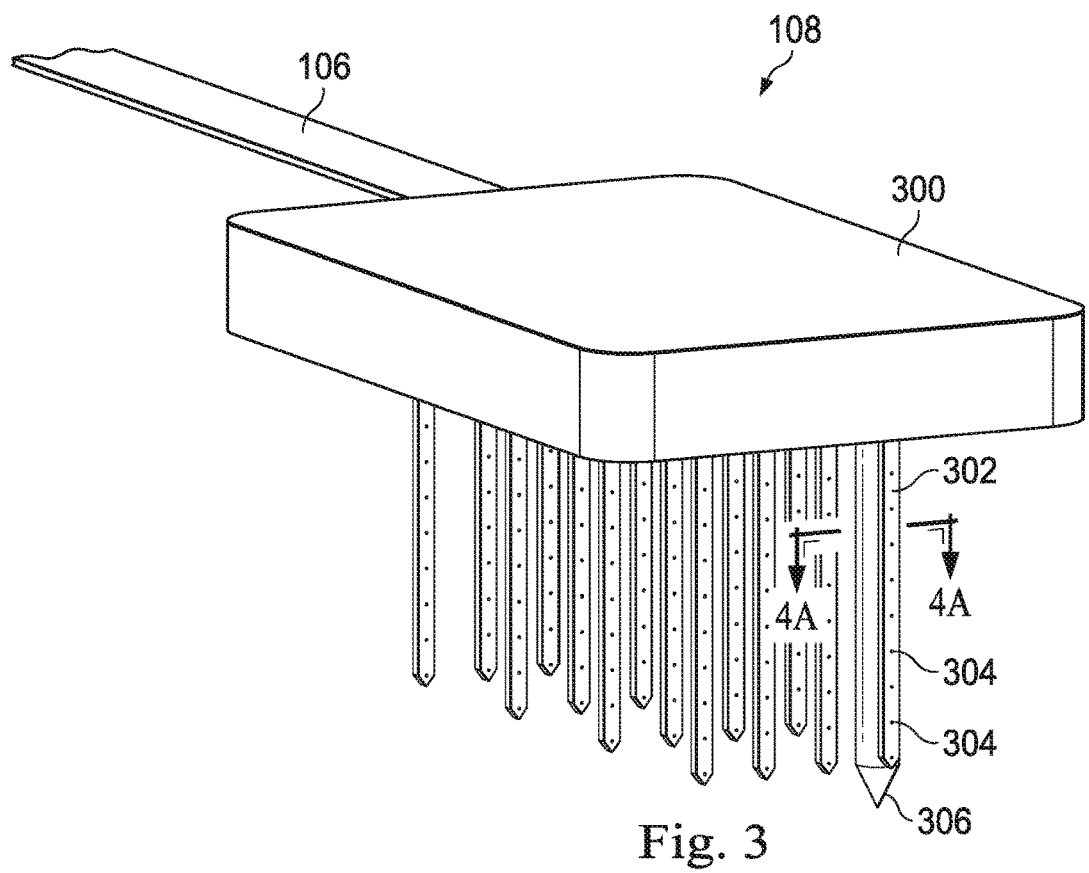
FIG. 3 is a perspective view of a neural probe electrode assembly according to the present invention.
Figure 4A:
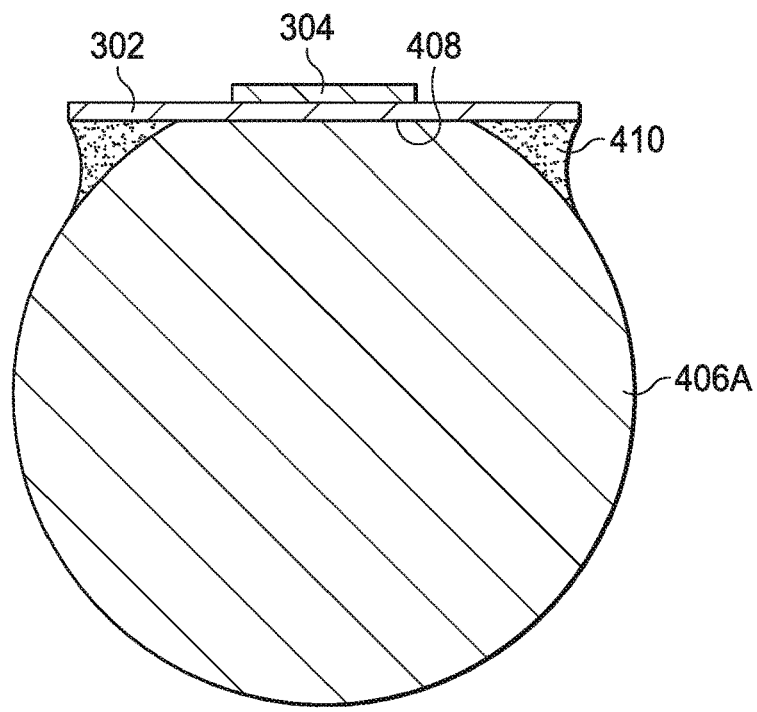
Figure 4B:
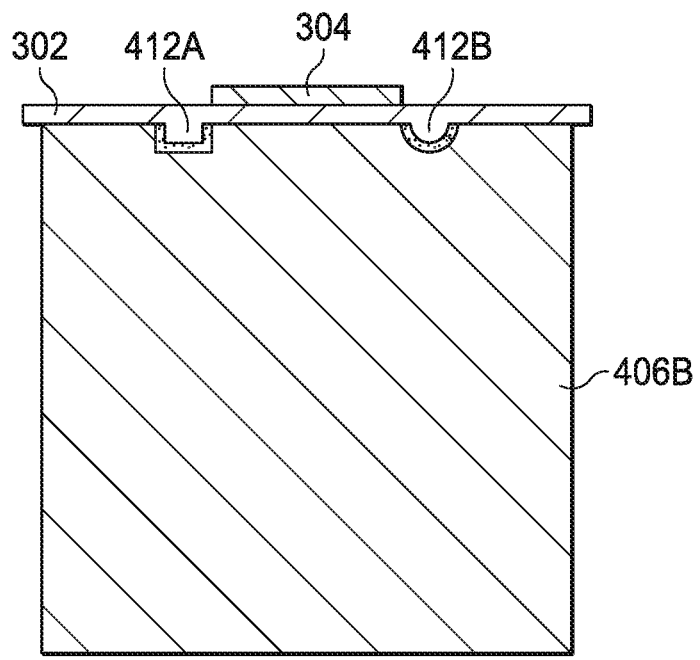
Figure 4C:
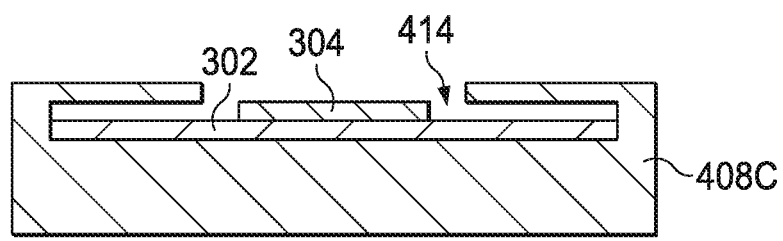

FIGS. 4A, 4B, and 4C are cross-sectional views of a neural probe as shown in FIG. 3, according to some embodiments of the present disclosure.

FIGS. 5A, 5B, and 5C are different perspective views of the neural probe embodiment of FIG. 4A, according to some embodiments of the present disclosure.

FIGS. 6A, 6B, and 6C are different perspective views of the neural probe embodiment of FIG. 4B, according to some embodiments of the present disclosure.

FIGS. 7A, 7B, and 7C are different perspective views of the neural probe embodiment of FIG. 4C, according to some embodiments of the present disclosure.

FIG. 8 includes another perspective view of another probe assembly, according to some embodiments of the present disclosure.

Figure 9A:
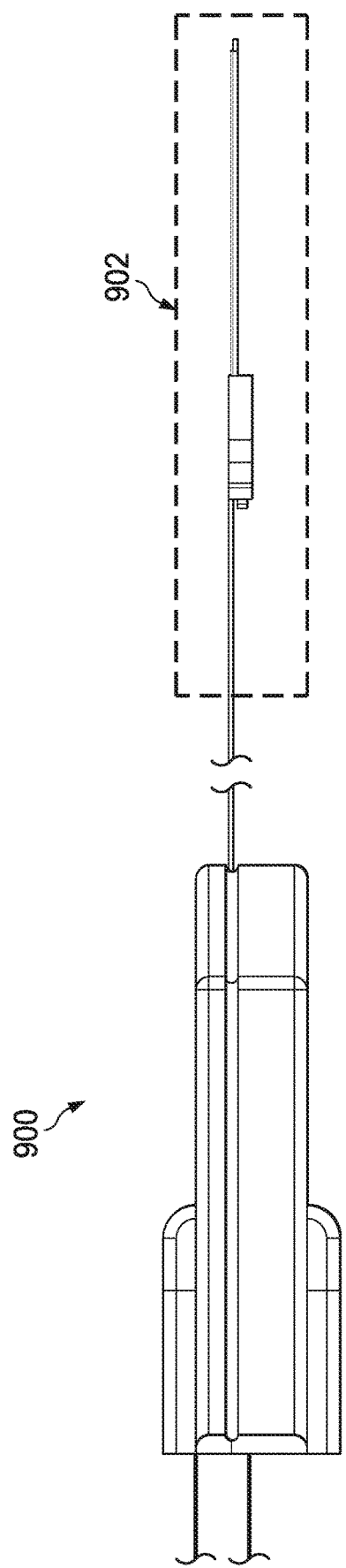
Figure 9B:
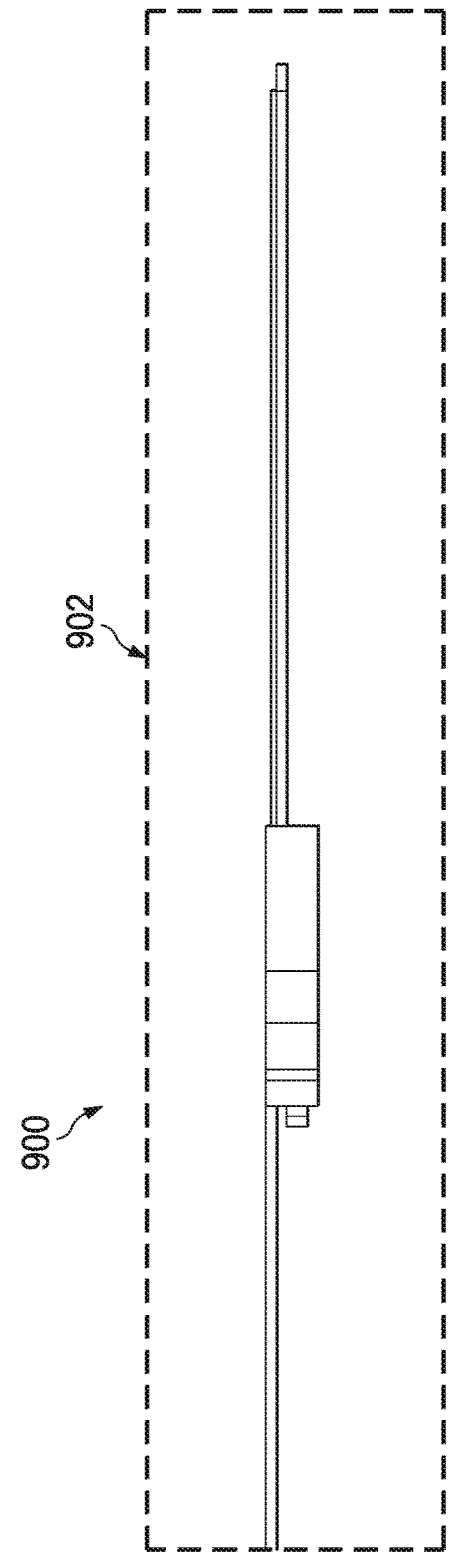

FIGS. 9A and 9B are three views of an exemplary probe assembly, according to some embodiments of the present disclosure.

Figure 10A:
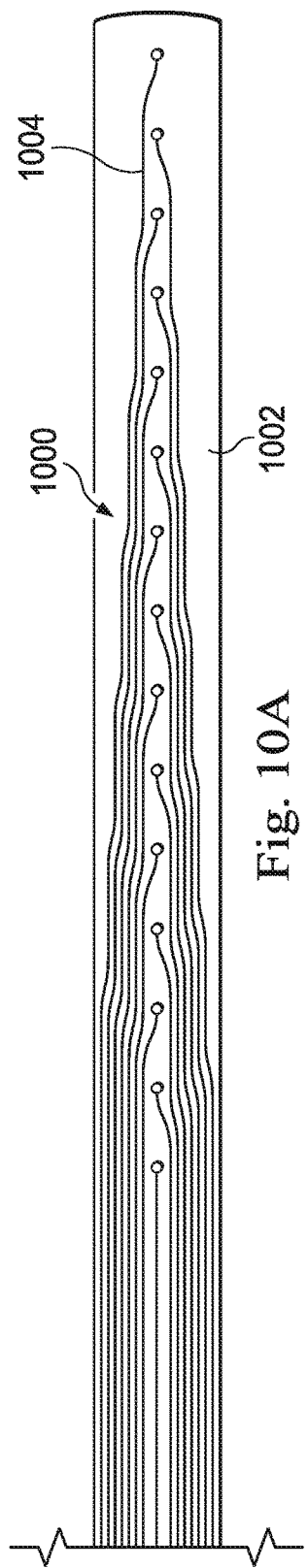

FIG. 10A shows a trace pattern extending along a length of a probe, according to some embodiments of the present disclosure.

Figure 10B:
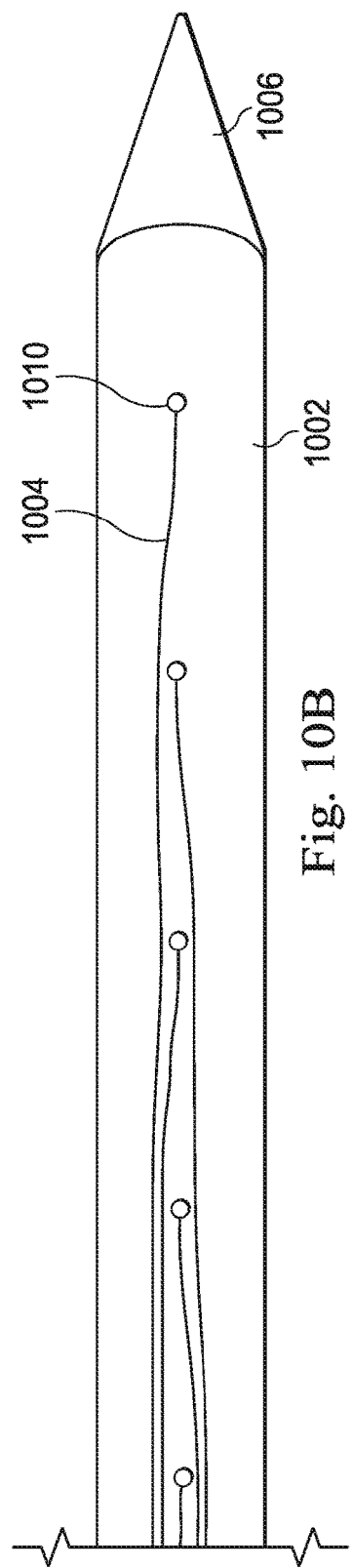

FIG. 10B provides a close-up view of a distal portion of the probe of FIG. 10A, according to some embodiments of the present disclosure.

Figure 10C:
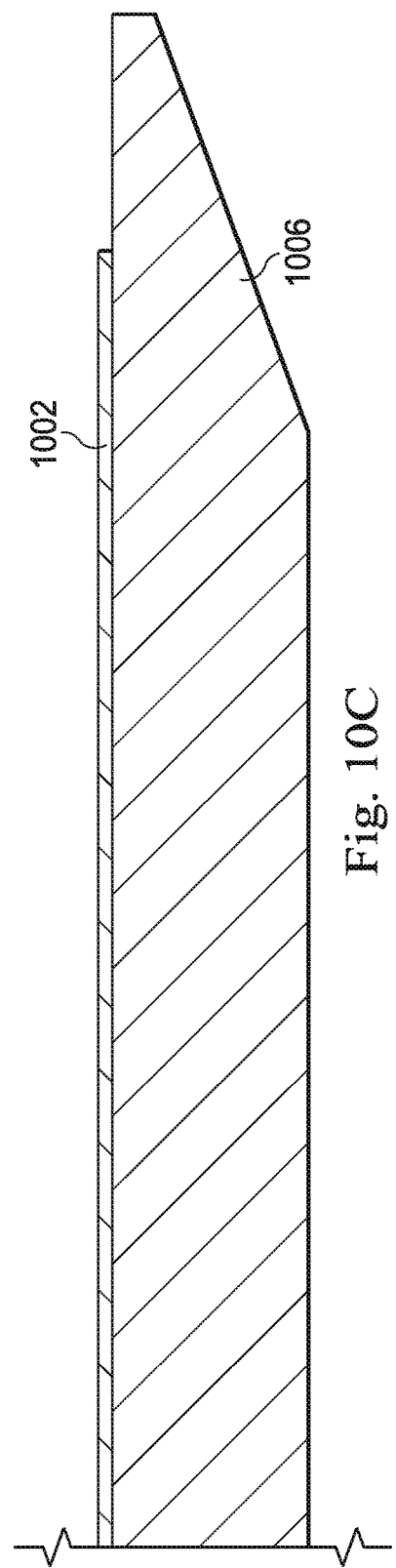

FIG. 10C shows a lateral view of the probe and the carrier of FIG. 10B, according to some embodiments of the present disclosure.

Figure 11A:
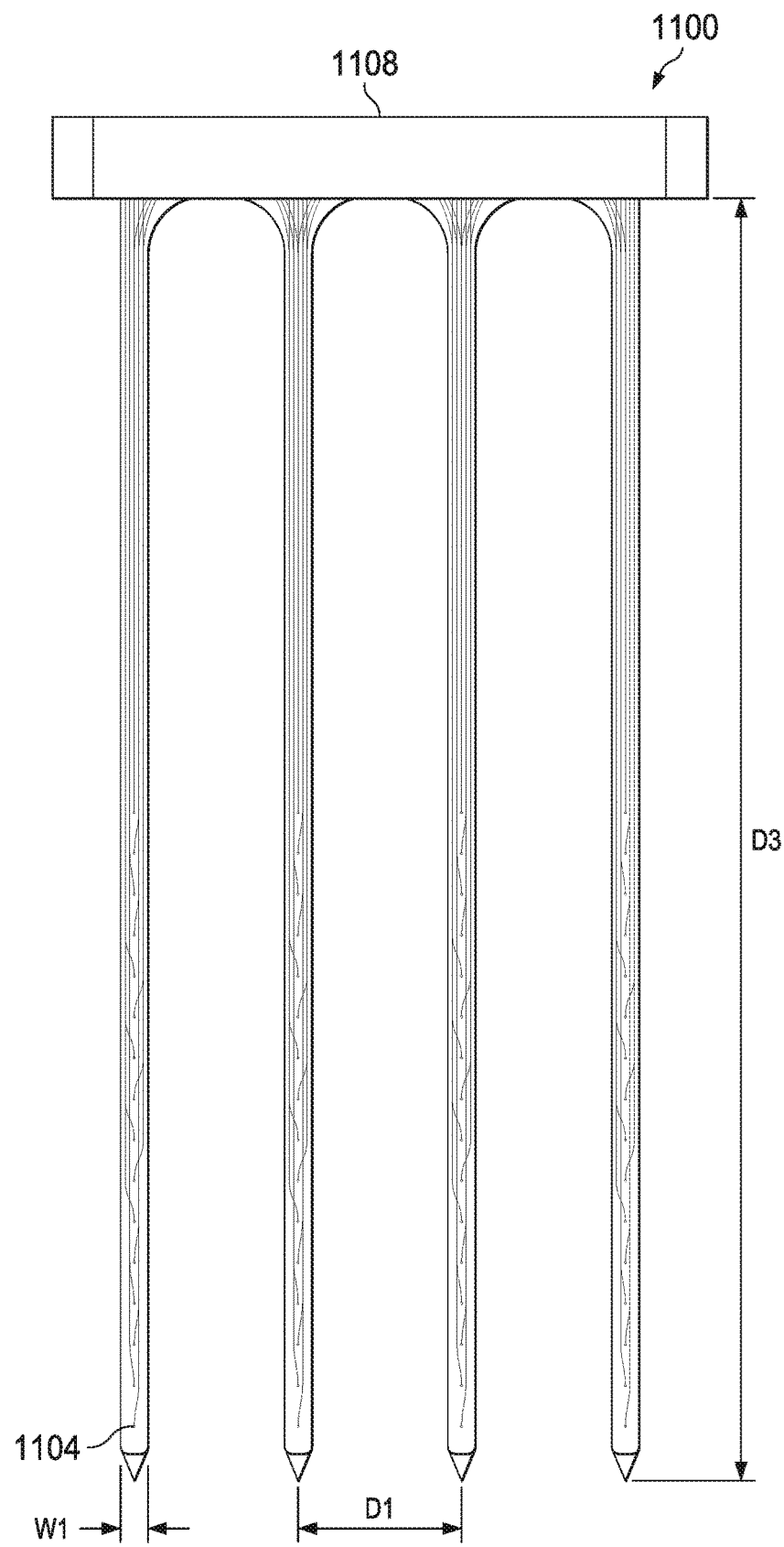
Figure 11B:
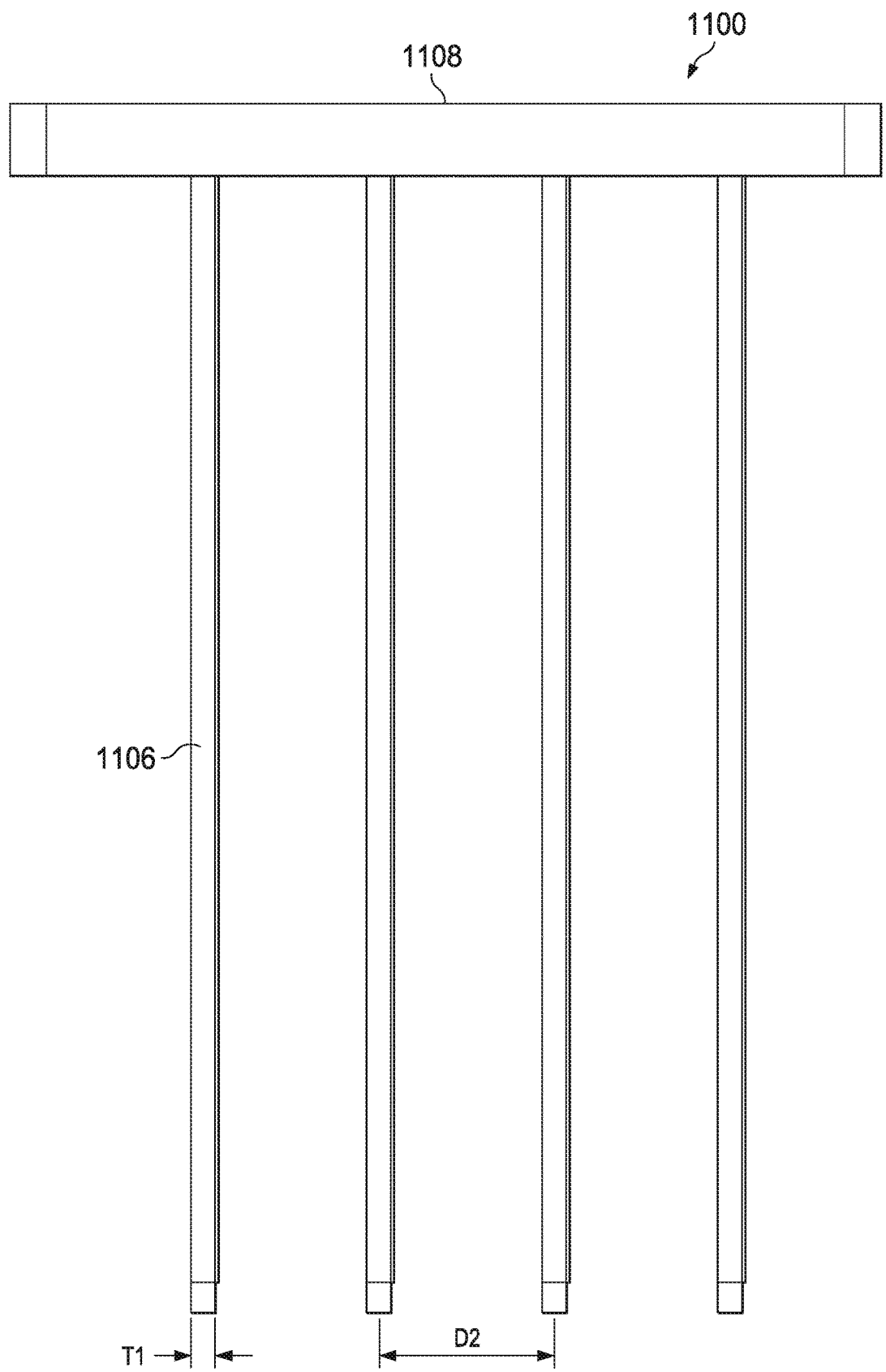
Figure 11C:
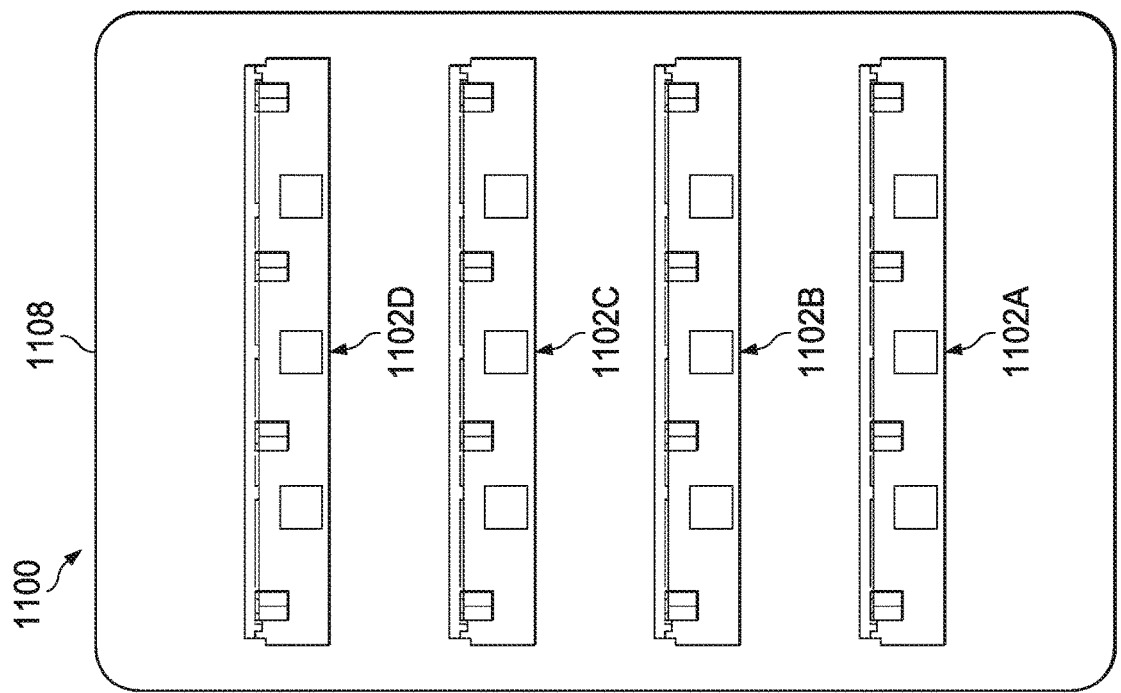

FIGS. 11A, 11B, and 11C depict views of two-dimensional probe arrays as combined in an electrode assembly, according to some embodiments of the present disclosure.

Figure 12:
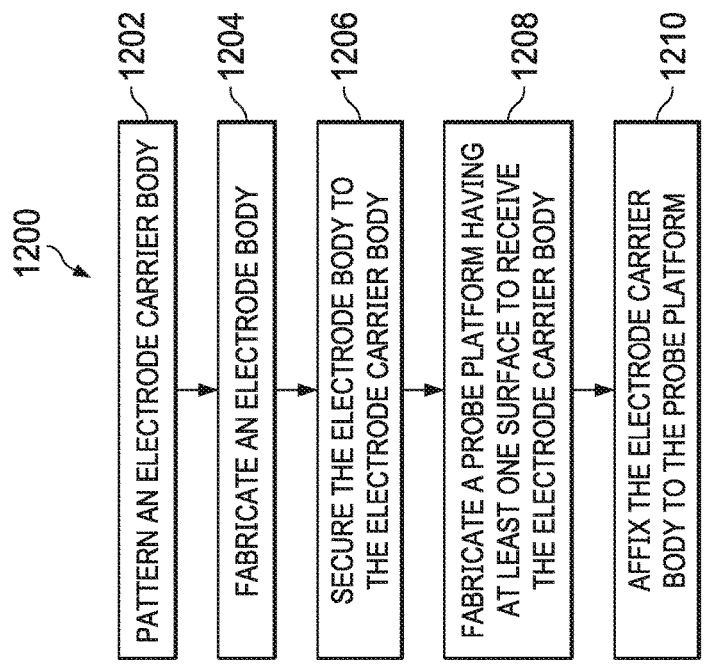

FIG. 12 is a flowchart of a method of fabricating a neural probe electrode assembly, according to some embodiments of the present disclosure.

These figures may be better understood by reference to the following detailed description.

DETAILED DESCRIPTION

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

The embodiments described herein recognize that is desirable to have systems and methods for inserting a high-quality, precise microelectrode array, which may allow bioelectrical and/or chemical interfacing, into mechanically tough tissues. Such tissues may be moving in complex ways. For example, the heart tissue is a mechanically touch tissue that may move in complex ways during blood circulation.

This detailed description discloses systems and methods for sensing and/or stimulation of bioelectrically active tissue in the body. By bringing electrodes into close contact with the nerves, the electrical signals produced by the nerves can be recorded and processed for research, diagnosis, and for interventional planning. Additionally, some embodiments of the present disclosure may include stimulation electrodes in addition to or as an alternative to recording electrode. The stimulation electrodes can be used to stimulate the tissues (e.g., nerves and/or muscles) in proximity to the electrodes. Such stimulation may be performed for diagnostic purposes as well as for therapeutic purposes. Embodiments of the present disclosure may be utilized to monitor and interact with a variety of tissues, and more particular to nerves within tissue. The term "neural" as used herein is not limited to referring to nerves in the brain, but refers to nerves or neurons in any anatomical structure or electrically active cells in any anatomical structure, such as myocytes in the heart.

The human nervous system includes a complex network of neurological structures that extend throughout the body. The brain interconnects with the spinal cord which branches into the brachial plexus near the shoulders and the lumbar plexus and sacral plexus in the lower back. The vagus nerve interfaces with the autonomous control of the heart, lungs, and digestive tract. The limb peripheral nerves of the arms extend distally from the brachial plexus down each arm. Similarly, the limb peripheral nerves of the legs extend distally from the lumbar plexus and sacral plexus. The peripheral nervous system provides an interface between the central nervous system and other anatomical structures like the muscular system.

Because of differences in the tissue at the target site for an electrode array, the insertion force may be modulated so that the surgeon can manage the insertion smoothly and reduce the likelihood of damaging the individual electrodes/probes and their associated circuitry and the target tissue. While some tissues, such as brain tissue may be relatively soft, yielding more easily to the insertion of electrodes, other tissues are more difficult. For example, cardiac tissue and neural tissue may be more difficult to penetrate. In certain cases, dura mater may need to be penetrated in order to access a softer target tissue. Cardiac tissues, which are largely muscular, can provide significantly more resistance to the insertion or implantation of electrodes. Embodiments of the present disclosure provide strong penetrating electrodes for insertion in such tissues.

Figure 1A:
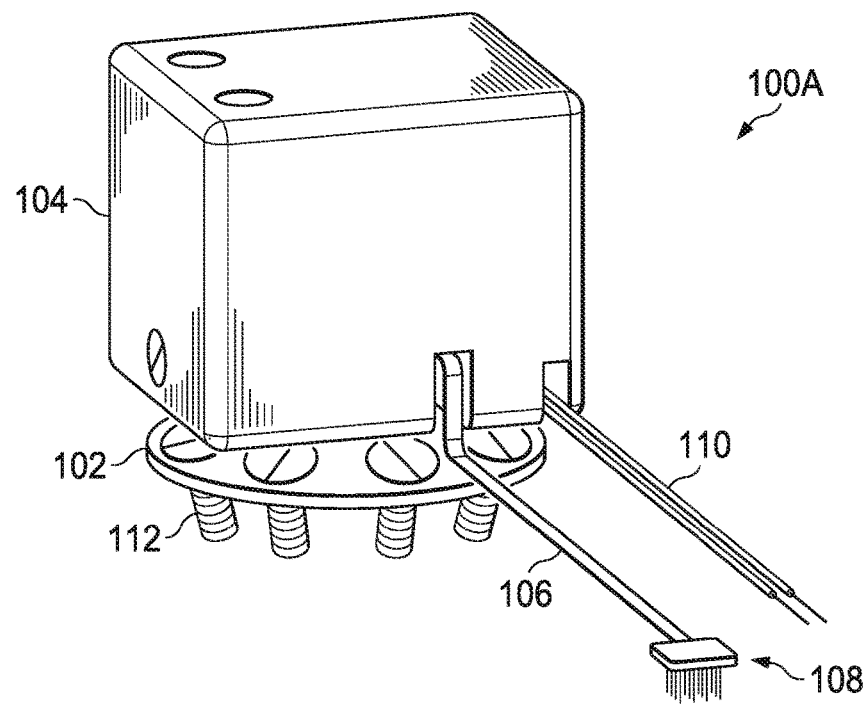
FIG. 1A is a perspective view of a neural probe electrode array system, according to some embodiments of the present disclosure.

Turning now to the drawings, FIG. 1A is a perspective view of a neural probe electrode array system 100A, according to the some embodiments of the present disclosure. The neural probe electrode array system 100A is a three-dimensional system. The neural probe electrode array system 100A comprises a mounting plate 102 supporting an electronics housing 104. A flexible ribbon cable 106 connects from electronics in the housing 104 to a neural probe electrode assembly 108. A neural probe electrode assembly 108 according to the present invention includes at least one, and preferably a plurality of neural probe electrode arrays. The depicted embodiments of the housing 104 further includes wires 110 extending therefrom. The wires 110 may include one or more wires and may provide for power, transmission of signals to or from the electrode assembly 108, and/or ground. These wires not only ground the subject, but also may be used as a reference when performing differential recording, or as a return path for current when stimulating tissue.

Figure 1B:
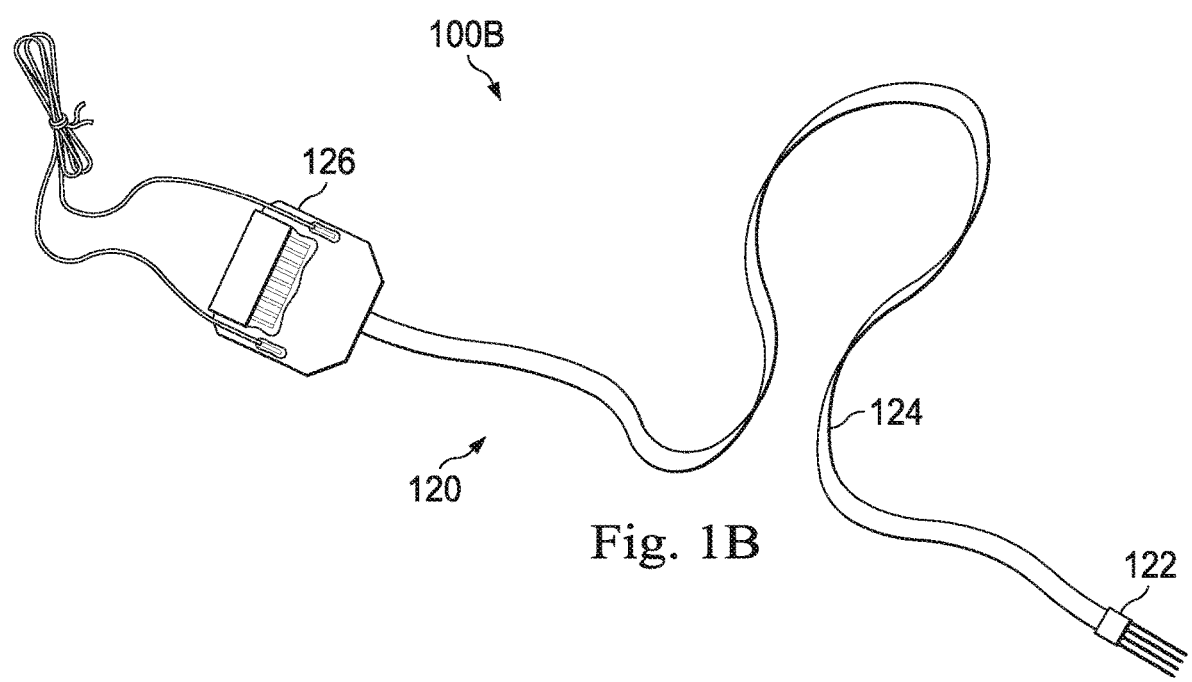
FIG. 1B is a view of a neural probe electrode array system, according to some embodiments of the present disclosure.

FIG. 1B is a view of a neural probe electrode array system 100B, according to some embodiments of the present disclosure. FIG. 1B includes another embodiment of the neural probe electrode assembly 120, which has two-dimensional electrode array 122 disposed at a distal end of a cable component 124 and a subcircuit 126 connected to the proximal end of the cable component 124. However, in some embodiments, a plurality of assemblies 120 like that shown in FIG. 1B may be combined together, such that multiple two-dimensional electrode arrays 122 are secured together to form a two-dimensional array. The subcircuits 126 may be disposed within a single housing, like the housing 104 of FIG. 1A. The cable component 124 may be joined together in the flexible ribbon cable 106 of FIG. 1A. As described herein, an electrode array system 100 or system 100 may refer to either the three-dimensional neural probe electrode array system 100A or the two-dimensional neural probe electrode array system 100B.

Figure 2A:
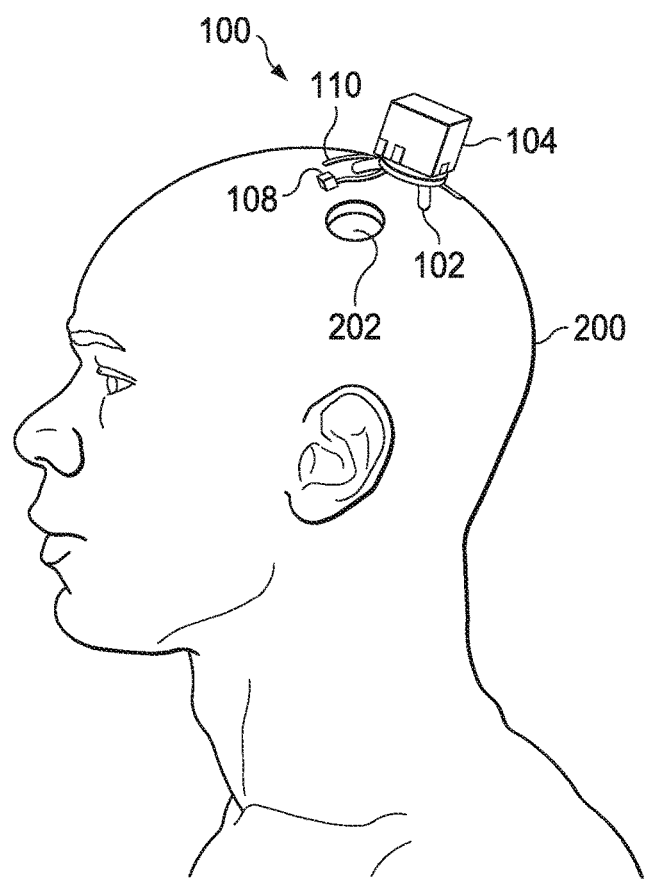
FIG. 2A is a perspective view of the neural probe electrode array system of FIG. 1 mounted to a skull in a cranial application of the system 100, according to some embodiments of the present disclosure.
Figure 2B:
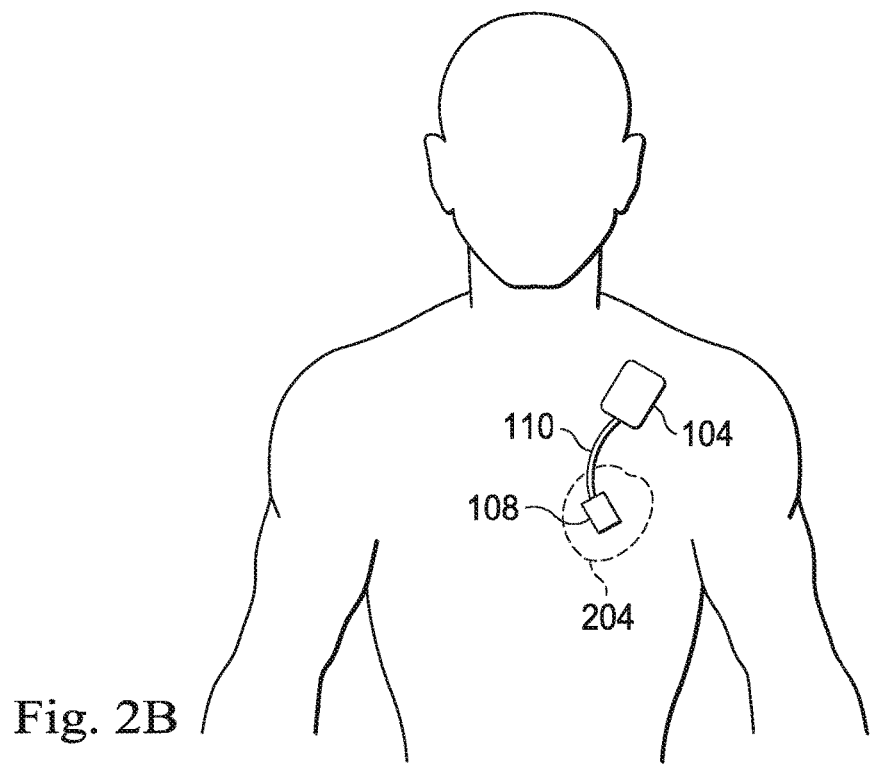
FIG. 2B is a top view of the neural probe electrode array system of FIG. 1 attached to a patient in a cardiac application of the system, according to some embodiments of the present disclosure.

Referring now to FIGS. 2A and 2B, shown therein are different applications of the neural probe electrode array system 100 of FIG. 1. FIG. 2A is a perspective view of the neural probe electrode array system 100 of FIG. 1 mounted to a skull 200 in a cranial application of the system 100, according to some embodiments of the present disclosure. The mounting plate 102 may be secured to the skull 200 by one or more fasteners 112, shown in FIG. 1. As depicted in FIG. 1, the fasteners 112 are screws. However other embodiments may use adhesive, clamps, bolts, or other fastening mechanisms to secure the mounting plate 102 (and thereby the housing 104) to a portion of patient anatomy. In such cranial applications, and opening 202 may be formed in the skull 200 of the patient to enable the individual electrodes of electrode assembly 108 to be positioned within the brain tissue.

FIG. 2B is a top view of the neural probe electrode array system 100 of FIG. 1 attached to a patient in a cardiac application of the system 100, according to some embodiments of the present disclosure. A surgeon can couple the electrode assembly 108 to the outside surface of the heart 204. The housing 104 can be affixed to another location on or in the patient, with the wires 110 extending between the housing at that location to the electrode assembly 108. When the surgeon attaches the electrode assembly 108 to the heart 204, pressure may be applied to the electrode assembly 108 so that individual electrodes and individual probes, which may have a needle like shape, are properly positioned below the exterior surface of the heart 204.

In some embodiments, the housing 104 may be integrated into the electrode assembly 108 so that the electronics and/or power supply contained in the housing 104 are positioned within the skull 200 or on the heart 204 along with the electrode assembly 108. Embodiments of the system 100 may be deployed in or on other parts of the body, in addition to those shown in FIGS. 2A and 2B.

FIG. 3 is an enlarged view of the electrode assembly 108 of FIG. 1, and shows a distal region of the flexible ribbon cable 106 connected to the neural probe electrode assembly 108. The ribbon cable 106 is designed to be flexible so that the neural probe electrode assembly 108 is can be positioned freely within the radius defined by the length of the ribbon cable 106 relative to the electronics housing 104. This allows the neural probe electrode assembly 108 to "float" with the brain during brain pulsation or brain shift or to "float" on the heart during cardiac cycling that pumps blood through the body of the patient. The ribbon cable 106 may be a thin-film based cable like those made from polyimide, parylene, or silicone with embedded conductors (e.g., gold, platinum, etc.). In some embodiments, the ribbon cable 106 may include a plurality of ribbon cables layered together into a single composite ribbon cable. In yet other embodiments, the ribbon cable 106 may include a plurality of ribbon cables arranged side-by-side on a flexible carrier cable. In embodiments with multiple ribbon cables included in the ribbon cable 106, each individual ribbon cable may be coupled to a single row or to another subset of the probes included in the neural probe electrode assembly 108.

The neural probe electrode assembly 108 comprises a probe platform 300 supporting one or more arrays of neural probe electrodes. In some embodiments, probes may consist of single- or multi-shank configurations where each shank may include linear or non-linear arrangements of electrode contacts. Multiple probes (single- or multi-shank) may be combined into a two-dimensional array of probes (resulting in a three-dimensional array of electrode contacts) to produce the neural probe electrode assembly 108 shown in FIG. 3. As shown in FIG. 3, the neural probe electrode assembly 108 includes four (4) total probe shank assemblies, like the exemplary probe shank 302, in a 4×4 matrix of shanks. In this example, the ribbon cable 106 may include four individual cable components bundled together. Embodiments of the probe platform 300 may include arrays and matrices of different dimensions. For example, one embodiment of the probe platform 300 may include a 2×10 matrix of shanks, while another embodiment includes a 6×7 matrix of shanks. Each of the shanks may include a plurality of individual electrode contacts like the electrode contacts 304 of probe shank 302. The depicted embodiment includes 16 electrode contacts 304, but other embodiments may include more or fewer. For example, some embodiments of the probe shank 302 include a single electrode contact 304 formed by or on the surface of the probe shank 302.

While in some embodiments, the probe platform 300 may be formed from a rigid material, the depicted probe platform 300 is formed from a flexible material that permits the probe platform 300 to deform. The deformation of the probe platform 300 permits the platform 300 to conform to the exterior surface of the portion of the body to be monitored and/or stimulated by the electrodes of the probe platform 300. Additionally, the deformation of the probe platform 300 may enable the individual probe shanks 302 to move toward each other or away from each other as the underlying tissue expands and contracts, flexes and relaxes. Like the ribbon cable 106, the probe platform 300 include a thin-film based substrate made from polyimide, parylene, or silicone with embedded conductors (e.g., gold, platinum, etc.) that electrically coupled to the probe shanks 302 and the individual electrodes 304 formed thereon.

Embodiments of the neural probe electrode assembly 108 may include one or more carriers or reinforcement structures to provide additional strength to the individual probe shanks 302 to enable the probe shanks 302 to be inserted into the muscular tissue of the heart 204. FIG. 3 depicts one such reinforcement structure or reinforcement carrier 306. As depicted, the carrier 306 includes a sharpened distal tip to facilitate insertion into the cardiac tissue. More specifically, the carrier 306 may effectively increase the rigidity of the probe shank 302. While the sharpened distal tip of the carrier 306 is depicted in FIG. 3 as protruding beyond the sharpened distal tip of the probe 302, other embodiments of the probe 302 may have a distal tip extending equally with or beyond the distal tip of the carrier 306.

FIGS. 4A, 4B, and 4C depict exemplary cross-sectional views of embodiments of probe/carrier combinations, according to some embodiments of the present disclosure. As shown in FIG. 4A, the probe 302, and the electrode 304 formed thereon, a couple lengthwise to a generally circular carrier 406A. The carrier 406A may include a flat surface, or simply a "flat," to facilitate the connection between the probe 302 and the carrier 406A. As shown in FIG. 4A, a portion of the probe 302 extends beyond the surface of the flat 408. In some embodiments, the flat 408 is formed such that it substantially matches, or extends beyond the width of the probe 302, in order to protect the probe 302 during insertion into cardiac tissue. As shown, the width of the probe 302 is approximately 80% of the diameter of the carrier 406A. Other embodiments may have a ratio ranging from 60% to 90%. In some embodiments, an adhesive 410 is used to attach and secure the probe 302 to the carrier 406A and may extend between the overhanging portions of the probe 302 and the exterior surface of the carrier 406A.

Carrier 406B may have a generally rectangular cross-sectional shape. As shown in FIG. 4B, some embodiments of the probe 302 and the carrier 406B may further include corresponding combinations of protrusions and slots. The protrusion/slot combinations may include similar shapes or different shapes. FIG. 4B shows a generally rectangular protrusion/slot combination 412A and a generally semicircular protrusion/slot combination 412B. The protrusion slot combinations 412 may be used to orient the probe 302 and the carrier 406B during an assembly step and may have an adhesive, like the adhesive 410, disposed therebetween to secure the probe 302 to the carrier 406B. Additionally, some embodiments of the protrusion/slot combinations may operate to secure the probe 302 to the carrier 406B by having a dovetail configuration or another suitable configuration. As shown, the width of the probe 302 is greater than the width of the carrier 406B. Embodiments of the carrier 406B may be greater than or equal to the width of the probe 302.

FIG. 4C depicts a cross section of a carrier 408C configured to receive the probe 302 in a longitudinal channel 414 formed therein. The longitudinal channel 414 may generally secure the probe 302, while exposing the electrode 304. Some embodiments may include portions of adhesive inserted in some of the unoccupied portions of the channel 414. Additionally, some embodiments of the probe 302 may include protrusions that extend upward from an upper surface of the probe 302, having a total thickness that substantially corresponds to the thickness of the channel 414, such that the protrusions further secure the probe 302 in place within the channel 414. The channel 414 may extend the full length or near the full length of the carrier 406C, and the opening to the channel 414 that exposes the electrode 304 may extend longitudinally to expose multiple electrodes or each electrode along the probe 302 may be aligned with an opening when the probe is fully inserted within the channel 414 of the carrier 406C.

As noted, FIGS. 4A-C depict cross-sectional embodiments of the carrier 306 of FIG. 3. Each of the carriers 406A, 406B, and 406C may include sharpened or pointed distal tips. The sharpened or pointed distal tips may have a tip that converges to a single point or a tip that converges to a line. While the electrode 304 is depicted in each of FIGS. 4A-C as projecting up from the top surface of the probe 302, other embodiments of the electrodes 304 may be formed flush with the top surface of the probe 302 or may be recessed therein. Additional carrier embodiments may include different shapes or variations of existing shapes, such as a generally rectangular cross-section with rounded corners or a generally semi-circular cross section.

Referring now to FIGS. 5A, 5B, and 5C, shown therein are different perspective views of the neural probe embodiment of FIG. 4A, according to some embodiments of the present disclosure. FIG. 5A is a top-down view of a probe assembly 500. The probe assembly 500 includes a plurality of probes like the exemplary probe shank 502, which is a fixed to a ruggedizing or rigidizing carrier 504. The probe assembly 500 includes a linear array of four such probes, rigidized for insertion into cardiac tissue to monitor or activate the cardiac tissue in proximity to the probe assembly 500. These probe shanks may be integrated into one thin film probe structure or, in some cases, may be individual thin film arrays. While the distal tips of the probes 502 and carriers 504 are sharpened, proximal ends of the probes and carriers 504 are coupled to a backend structure 506. In some embodiments, the backend 506 includes slots configured to receive each of the probes 502 and/or each of the carriers 504. As shown in the perspective view of FIG. 5C, the exemplary slot 508 is configured to receive the proximal ends of the carrier 504 and the probe shank 502 such that the top surface of the probe shank 502 does not extend above a top surface of the backend 506. In some embodiments, the top surface of the probe shank 502 is coplanar with the top surface of the backend 506. The backend 506 may be made from a rigid material such as silicon, silicon oxide, or a biocompatible polymer or metal. In some embodiments, the backend 506 may be etched and/or machined to produce the slots 508.

Referring now to FIGS. 6A, 6B, and 6C, shown therein are different perspective views of the neural probe embodiment of FIG. 4B, according to some embodiments of the present disclosure. FIG. 6A is a top-down view of a probe assembly 600. The probe assembly 600 includes a plurality of probe shanks like the exemplary probe shank 602, which is a fixed to a ruggedizing or rigidizing carrier 604. The probe assembly 600 includes a linear array of four such probe shanks, rigidized for insertion into cardiac tissue to monitor or activate the cardiac tissue in proximity to the probe assembly 600. These probe shanks may be integrated into one thin film probe structure or, in some cases, may be individual thin film arrays.

As depicted in FIG. 6B, the distal tip of the carrier 604 has a beveled surface angled toward the bottom surface of the probe shank 602. Proximal ends of the probes 602 and carriers 604 are coupled to a backend structure 606. In some embodiments, the backend 606 includes slots configured to receive each of the probes 602 and/or each of the carriers 604. As shown in the perspective view of FIG. 6C, the exemplary slot 608 is configured to receive the proximal ends of the carrier 604 and the probe shank 602 such that the top surface of the probe shank 602 does not extend above a top surface of the backend 606. One or more rails, tabs, or lips 612 may protrude above the top surface of the backend 606 in some embodiments. Additionally, in some embodiments, the top surface of the probe shank 602 is coplanar with the top surface of the backend 606. The backend 606 may be made from a rigid material such as silicon, silicon oxide, or a biocompatible polymer or metal. In some embodiments, the backend 606 may be etched and/or machined to produce the slots 608. The combined structure of the probe shank 602 and the carrier 604 may be affixed to the backend 606 by an adhesive, by a micro-welding operation or by a fusion process, such as exposure to heat exceeding a threshold at which the material of the surface of the slots 608 in the backend 606 fuses into the material of the carrier 604 and/or the probe shank 602. In other embodiments, the backend 606 and the carriers 604 are formed integrally.

Referring now to FIGS. 7A, 7B, and 7C, shown therein are different perspective views of the neural probe embodiment of FIG. 4B, according to some embodiments of the present disclosure. FIG. 7A is a top-down view of a probe assembly 700. The probe assembly 700 includes a plurality of probes like the exemplary probe shank 702, which is affixed to a channel extending with the ruggedizing or rigidizing carrier 704. The probe assembly 700 includes a linear array of such probes, rigidized for insertion into cardiac tissue to monitor or activate the cardiac tissue in proximity to the probe assembly 700. Proximal ends of the probes 702 and carriers 704 are coupled to a backend structure 706. One or more lips 712 may protrude above the top surface of the backend 606 in some embodiments. In some embodiments, the backend 706 includes slots configured to receive each of the probes 702 and/or each of the carriers 704. As shown in the perspective view of FIG. 7C, the exemplary slot 708 is configured to receive the proximal ends of the carrier 704 and the probe shank 702 such that the top surface of the probe shank 702 does not extend above a top surface of the backend 706. In some embodiments, the top surface of the probe shank 702 is coplanar with the top surface of the backend 706. The backend 706 may be made from a rigid material such as silicon, silicon oxide, or a biocompatible polymer or metal. In some embodiments, the backend 706 may be etched and/or machined (such as by electrostatic discharge machining, laser ablation, etc.) to produce the slots 708. The combined structure of the probe shank 702 and the carrier 704 may be affixed to the backend 706 by an adhesive, by a micro-welding operation or by a fusion process, such as exposure to heat exceeding a threshold at which the material of the surface of the slots 708 in the backend 706 fuses into the material of the carrier 704 and/or the probe shank 702.

Each of the backend mechanisms 506, 606, and 706 may include circuitry and/or electrical traces that may be coupled to a component of the flexible ribbon cable 106. Some backend embodiments may further include a bond pad grid or ball grid array to couple traces extending along the probe shanks to corresponding traces extending along the flexible ribbon cable 106. In some embodiments, the traces extend continuously from the electrodes on the probe shanks to the housing 104. Accordingly, some embodiments of the backend mechanisms may be formed from printed circuit boards (PCBs).

The 1×4 probe shown in FIGS. 5A-C, 6A-C, and 7A-C, may be combined with other probes in a single probe platform like the probe platform 300 of FIG. 3, or may be used without a probe platform. In such an embodiment, the probe platform 300 may include combinations of the probes and carriers depicted in FIGS. 5A-C, 6A-C, and 7A-C. For example, a single probe platform 300 may include the probe assembly 500, the probe assembly 600, and the probe assembly 700, with their respective probes and carriers. In some embodiments, a probe assembly may include one or more single-shanked probes, such as included in probe assemblies 500, 600, and 700. In other embodiments, a probe assembly may include one or more multi-shanked probes (e.g., a 4×4 probe, an 8×4 probe, etc.).

Additionally, in some embodiments of the probe assemblies 500, 600, and/or 700, the carrier may be formed integrally with the backend 506, 606, and/or 706. In such embodiments, the top surface of the carrier is flush with the corresponding backend. In these and other embodiments, the backend may include one or more lips or etch components that extend upward from the top surface of the backend mechanism to receive electrical traces connected to the electrodes. For example, FIG. 5A depicts a lip 512 protruding upward along lateral edges of the backend 506. Similar lips are depicted in FIGS. 6C and 7D, among other figures. The lips may protrude a distance that corresponds to a thickness of a ribbon cable or flexible substrate that supports traces connecting to the electrodes on a probe assembly.

FIG. 8 includes another perspective view of a probe assembly 800, having a plurality of probe shanks like the probe shanks 802, supported by a carrier 804 and a backend 806. The probe shanks 802 are organized as multi-shanked probes, each supported by a different extension of carrier 804. As one example, each of the probes may be formed by 4, 6, 8, 10, 13, or some other number of shanks. The carrier 804 and the backend 806 are formed integrally. The backend 806 includes two bordering lips 812, which help to secure a thin-film interconnect 810. The thin-film interconnect 810 may be separate or integrated with the probe assembly 800. The thin-film interconnect 810 may include the leads and traces extending along the probe shanks 802 to connect to the electrodes thereon to circuitry for signal processing. Additionally, the thin-film interconnect 810 may form a portion of the ribbon cable 106 of FIG. 1. The width of the thin-film interconnect 810 may be about 3.5 mm in some embodiments, but may range from about 1 mm to about 10 mm depending on the number of an separation distance between traces.

The probes and ruggedizing characters depicted herein may range in sizes that are suitable for use in monitoring and/or stimulating biological tissue. For example, while the distance D1 between adjacent probes in an individual probe assembly component may be about 1 mm in certain embodiments, the distance D1 may range from about 0.1 mm to about 2 mm in other embodiments. Similarly, the distance D2 between adjacent probes in adjacent probe assembly components may be about 1 mm in certain embodiments. This distance D2 may similarly range from about 0.2 mm to about 2 mm in other embodiments. The length of the probes may also vary from embodiment to embodiment. As shown the length of the probe (illustrated by distance D3 in FIG. 11B) may be about 8 mm. Other embodiments of the probes may range from 1 mm to about 15 mm in length. The backend of probe assembly components may have a length of about 2 mm in some embodiments and a length of about 0.5 mm in other embodiments or another length there between. Embodiments of the probe shanks may have a width W1 ranging from about 0.05 mm to about 0.4 mm. As illustrated in FIG. 11B, the width W1 may be about 0.150 mm.

FIGS. 9A and 9B are two views of an exemplary probe assembly 900 and includes associated dimensions of a particular embodiment. FIG. 9B is an enlarged view of portion 902 of probe assembly 900. In these embodiments, the width W1 of the probe shank may be less than the length of the probe shank. In other embodiments, the width W1 is greater than the length of the probe shank (distance D3). Some of these dimensions are referred to in connection with the description of FIG. 11, below.

FIG. 10A shows a trace pattern 1000 extending along a length of a probe 1002. The individual traces 1004 are coupled to each of the electrodes 1010, which are distributed along the length of the probe 1002. The electrodes 1010 may be configured in any two-dimensional manner. For example, the electrodes 1010 may be distributed in a linear configuration, in a configuration of two staggered or not staggered rows, in a configuration of three staggered or not staggered rows, a configuration of some other number of staggered or unstaggered rows, or some other type of configuration.

The traces 1004 may be patterned such that the overall group of traces has a triangular shape, pointing toward the distal end of the probe 1002. The may keep the traces 1004 away from the edges of the probe 1002 at the distal end thereof. FIG. 10A provides a close-up view of a distal portion of the probe 1002, coupled to a carrier 1006. In this depicted embodiment, the distal end of the probe 1002 is slightly rounded and is not sharpened or pointed. However, in FIG. 10B, the carrier 1006 is sharpened or pointed to facilitate insertion into the tough tissues of the cardiac muscle or other tougher tissues of a patient. FIG. 10C shows a lateral view of the probe 1002 and the carrier 1006, and further shows the relative thicknesses of the probe 1002 and the carrier 1006. In some embodiments, the carrier 1006 may be more than ten times as thick as the probe 1002. In FIG. 10C, the distal end of the carrier 1006 is sharpened or pointed and is tapered such that a thickness of the carrier 1006 decreases in a direction towards the distal end of the carrier 1006. The sharpening and tapering of the distal end of the carrier 1006 may facilitate insertion of the carrier 1006 and thereby, the probe 1002, into tough tissues.

FIGS. 11A, 11B, and 11C depict views of two-dimensional probe arrays 1102A, 1102B, 1102C, and 1102D as combined in an electrode assembly 1100. FIG. 11A shows a front view of the electrode assembly 1100, such that electrodes and traces on the probes 1104 of probe array 1102A are depicted. FIG. 11B shows a side view of the two-dimensional arrays 1102 of the electrode assembly 1100, while FIG. 11C shows a top view thereof. As shown in FIG. 11B, carriers 1106 may have thickness T1.

The top view of 1100C depict bond pads and other structures that may be disposed on a top surface of the probe arrays 1102 for coupling to one or more ribbon cables included in the flexible ribbon cable 106 of FIG. 1. While the probes 1104 and carriers 1106 of the arrays 1102 extend orthogonally to a bottom surface of the probe platform 1108, other embodiments of the probe platform 1108 may include slots disposed at an angle within the body of the probe platform 1108 such that the probes 1104 and carriers 1106 extend and an angle relative to the bottom surface of the probe platform 1108. For example, the probes and carriers may form an angle ranging from 25° to 75°.

FIG. 12 is a flowchart of a method 1200 of fabricating a neural probe electrode assembly, according to some embodiments of the present disclosure. The method 1200 is depicted as a series of enumerated steps or operations. Embodiments of the method 1200 may include additional operations before, after, in between, or as part of the enumerated operations. Additionally, the enumerated operations may be performed in a sequence other than that depicted in FIG. 12. For example, in some embodiments of the method 1200, the operation 1204 may be performed prior to the operation 1202.

As depicted, and embodiment of the method 1200 may begin at operation 1202 in which an electrode carrier body is patterned or manufactured. As noted herein, the electrode carrier body may be formed from a plurality of materials, including metals such as stainless steel, gold, platinum, etc. In other embodiments, the electrode carrier body may be formed from a rigid polymeric material. Forming the electrode carrier body may be produced by milling or micromachining a block of material. For example, electrical discharge machining or electrostatic discharge machining may be used to remove material from a block to reveal the electrode carrier body having a backend structure, like those described herein in connection with FIGS. 5A-C, 6A-C, 7A-C, 8, etc. The carrier body may further include elongate shanks or electrode carriers which are configured to support elongate probe shank structures also described herein in connection with FIGS. 5A-C, 6A-C, 7A-C, 8, 10A-C, etc. Additionally, the electrode carrier body may be molded by injection molding or another molding process. In some embodiments, the electrode carrier body is produced as a monolithic structure, as is shown in FIG. 8. In other embodiments, the electrode carrier body may be produced as a composite structure by manufacturing a backend block having holes or slots therein configured to receive separately manufactured carriers. For example, in some embodiments rigid wires may be cut separately and be connected at a proximal end thereof to the electrode carrier body backend block. The wires may be abutted against and welded onto a surface of the backend block or the wires may be inserted into corresponding slots and welded or otherwise secured in place, by press fitting or an adhesive for example. Additionally, lips may be formed in the backend block as described in connection with FIGS. FIGS. 5A-C, 6A-C, 7A-C, 8. In some embodiments, a milling or machining operation may be performed on one side of the block of material to form the general outline of the backend and the carriers. Another milling or machining operation may be performed on the opposite side of the block material to form the lips. Additional embodiments of the operation 1202 may be accomplished by 3D printing processes or other additive manufacturing processes rather than subtractive processes.

At operation 1204, an electrode body is fabricated. As described herein, the electrode body may be an elongate probe shank having one or more electrode contacts disposed on a surface thereof and having traces, wires, or lines extending from the electrode back to the proximal end of the probe. For example, the probe 1002 shown in FIGS. 10A-C (or another other probe described herein) may be fabricated by forming an elongate probe shank base structure, which may be formed from an insulating material or may be covered in an insulating material. Electrodes and traces may be formed by photolithography and/or deposition processes. Some processes may be similar to those described in U.S. patent application Ser. No. 14/519,583, entitled "Neural Electrode System With A Carrier Having A Tape Spring Type Shape," and filed Oct. 21, 2014, the disclosure of which is incorporated herein by reference in its entirety. Additionally, some embodiments of the present disclosure may include processing steps described in U.S. Pat. No. 8,561,292, entitled "Method For Manufacturing An Implantable Electronic Device," filed Nov. 16, 2009, the disclosure of which is incorporated herein a reference in its entirety. Accordingly, many different fabrication techniques may be used to produce the electrode body. Other techniques may be found in U.S. Pat. No. 7,941,202, entitled "Modular Multi-channel Microelectrode Array And Methods Of Making Same," filed Oct. 10, 2006, granted May 10, 2011, the disclosure of which is incorporated herein a reference in its entirety.

At operation 1206, the electrode body is secured to the electrode carrier body. For example, the probe 1002 of FIG. 10A may be secured to the carrier 1006. In some embodiments, this may be performed by applying an adhesive to either or both of the probe 1002 and the carrier 1006. Additionally, some embodiments of the operation 1206 may include aligning the electrode body with the electrode carrier body. This may be facilitated by the inclusion of a protrusion and groove combination, such as those described herein in connection with FIG. 4B. And as shown and described in connection with FIG. 4C, some embodiments of the operation 1206 may include inserting the electrode body into a channel formed within the electrode carrier body. Adhesion, fusion, welding, and/or friction may be used in some embodiments. The adhesive used may be an ultraviolet curing adhesive or a heat-curing adhesive. In such embodiments, the structures may be subjected to an ultraviolet radiation source or a heat source to assist in curing of the adhesive.

At operation 1208, and electrode platform may be fabricated. The electrode platform may have at least one surface, channel, or cavity configured to receive the electrode carrier body. The electrode carrier body may be received into the electrode platform after the electrode body has been secured to the electrode carrier body. As an example, FIG. 11C depicts multiple probe assemblies or arrays 1102 that are positioned within channels formed in the body of the probe platform 1108. The probe platform may be formed by a molding, printing, or machining process. The electrode carrier body may be secured to the probe platform by a press fit, application of an adhesive, etc., at operation 1210.

Embodiments of the method 1200 may further include securing flexible cables to individual arrays, like the arrays 1102, bundling the flexible cables into a single flexible cable, connecting traces extending along the flexible cables to electronics in a backend housing, and securing the housing to the cable or cables. In this way neural probe electrode assemblies as described herein can be manufactured.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

Embodiments of the present disclosure may enable delicate, flexible electrode arrays to be inserted into harder body tissues, such as cardiac tissue and neural tissue. More particularly, embodiments of the present disclosure may enable electrode arrays that have structural integrity to penetrate brain tissue to penetrate into cardiac tissue. Other tissues that are more difficult to penetrate may also be more easily accessed by embodiments of the present disclosure.

What is claimed is:

1. A ruggedized penetrating electrode array system comprising:
    a probe assembly comprising:
        one or more elongate shanks having one or more electrodes disposed on at least one exterior surface thereof;
        a backend structure,
            wherein the backend structure has a length, a width, and a thickness;
            wherein the backend structure has a top surface and an opposing bottom surface, wherein a distance between the top surface and the opposing bottom surface defines the length;
            wherein the backend structure has a first side and an opposing second side, wherein the first side is orthogonal to the top surface and the opposing bottom surface, and wherein a distance between the first side and the opposing second side defines the width;
            wherein the length and the width define a plane;
            wherein the length and the width are greater than the thickness of the backend structure;
            wherein the backend structure has a plurality of slots located in the opposing bottom surface;
            wherein a proximal end of each elongate shank of the one or more elongate shanks is received within a different, corresponding slot of the plurality of slots in the backend structure and is affixed to the backend structure; wherein the one or more elongate shanks are parallel to the plane; and
        an elongate carrier secured to the backend structure and extending away from the backend structure toward a distal end of one of the one or more elongate shanks, the elongate carrier being more rigid than the one or more elongate shanks.

2. The array system of claim 1, wherein the backend structure and the elongate carrier are integrally formed.

3. The array system of claim 1, wherein a proximal portion of the elongate carrier is inserted into a slot of the plurality of slots formed in the backend structure.

4. The array system of claim 1, wherein the one or more elongate shanks further comprise a plurality of elongate shanks and a plurality of elongate carriers, wherein the plurality of elongate shanks each has a corresponding elongate carrier of the plurality of elongate carriers.

5. The array system of claim 1, wherein the backend structure further includes at least one lip protruding up from the top surface of the backend structure.

6. The array system of claim 5, wherein the at least one lip has a thickness substantially equivalent to a thickness of a thin-film interconnect structure.

7. The array system of claim 6, wherein the thin-film interconnect structure is coupled to a flexible cable extending to a backend electronics housing.

8. The array system of claim 1, wherein the backend structure is a monolithic structure that defines walls of the plurality of slots; wherein the top surface of the backend structure is coplanar with the top surface of at least one of the one or more elongate shanks; and wherein the backend structure is secured to a probe platform.

9. The array system of claim 1, wherein the backend structure has a slot of the plurality of slots that receives the proximal end of an elongate shank of the one or more elongate shanks and a proximal end of the elongate carrier and wherein a distal end of the elongate carrier is tapered such that a thickness of the elongate carrier decreases in a direction towards the distal end of the elongate carrier.

10. The array system of claim 1, wherein the one or more elongate shanks include two elongate shanks that are received within two respective slots of the plurality of slots.

11. The array system of claim 1, wherein the one or more elongate shanks include three elongate shanks that are received within three respective slots of the plurality of slots.

12. The array system of claim 1, wherein the one or more elongate shanks include four elongate shanks that are received within four respective slots of the plurality of slots.

13. The array system of claim 1, wherein the backend structure is a monolithic structure that is at least one of etched or machined to define the plurality of slots.

14. A neural probe electrode system comprising:
    a probe platform configured to receive at least one probe array;
    a first probe array having a first plurality of probes,
        wherein a probe of the first plurality of probes is supported by a elongate carrier of a plurality of elongate carriers that is more rigid than the probe of the first plurality of probes; and
    a backend structure coupled to proximal ends of the first plurality of probes,
        wherein the backend structure has a length, a width, and a thickness;
        wherein the backend structure has a top surface and an opposing bottom surface, wherein a distance between the top surface and the opposing bottom surface defines the length;
        wherein the backend structure has a first side and an opposing second side, wherein the first side is orthogonal to the top surface and the opposing bottom surface, and wherein a distance between the first side and the opposing second side defines the width;
        wherein the length and the width define a plane;
        wherein the length and the width are greater than the thickness of the backend structure;
        wherein the backend structure has a plurality of slots located in the opposing bottom surface;
        wherein the backend structure has a plurality of slots located in the opposing bottom surface, each slot of the plurality of slots receives a proximal end of a different, corresponding probe of the first plurality of probes and a proximal end of the elongate carrier of the plurality of elongate carriers supporting the corresponding probe of the first plurality of probes;
        wherein at least one of the first plurality of probes are parallel to the plane; and
    wherein the elongate carrier of the plurality of elongate carriers is secured to the backend structure.

15. The system of claim 14, wherein the backend structure includes at least one lip to define a channel through which a thin-film interconnect extends, and wherein the channel is defined by the backend structure and the probe platform.

16. The system of claim 14, wherein the probe of the first plurality of probes has a first protrusion that is generally semi-circular and a second protrusion that is generally rectangular, the elongate carrier has a flat surface, and the probe of the first plurality of probes is fixed to the flat surface.

17. The system of claim 14 wherein the elongate carrier includes a pointed distal end that extends beyond a distal end of the probe.

18. The system of claim 14, wherein a thickness of the elongate carrier is around 10 times greater than a thickness of the probe.

19. The system of claim 14, wherein the probe of the first plurality of probes includes a protrusion on a back side of the probe, the protrusion configured to mate with a groove on a meeting surface of the elongate carrier.

\* \* \* \* \*